(12) United States Patent
Kheradvar et al.

(10) Patent No.: US 12,226,272 B2
(45) Date of Patent: Feb. 18, 2025

(54) SYSTEM FOR IRRIGATING THE UPPER AERODIGESTIVE TRACT AND NEIGHBORING AREAS

(71) Applicant: THE REGENTS OF THE UNIVERSITY OF CALIFORNIA, Oakland, CA (US)

(72) Inventors: Arash Kheradvar, Irvine, CA (US); Hamid R. Djalilian, Orange, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 882 days.

(21) Appl. No.: 17/381,831

(22) Filed: Jul. 21, 2021

(65) Prior Publication Data

US 2022/0023020 A1  Jan. 27, 2022

Related U.S. Application Data

(60) Provisional application No. 63/055,059, filed on Jul. 22, 2020.

(51) Int. Cl.
| | |
|---|---|
| A61C 17/02 | (2006.01) |
| A61B 1/24 | (2006.01) |
| A61M 3/02 | (2006.01) |

(52) U.S. Cl.
CPC ............ *A61C 17/0202* (2013.01); *A61B 1/24* (2013.01); *A61C 17/0211* (2013.01); *A61M 3/02* (2013.01); *A61C 2204/002* (2013.01)

(58) Field of Classification Search
CPC ... A61C 17/0202; A61C 17/028; A61C 17/02; A61C 17/024; A61C 17/0217; A61C 17/0211; A61C 17/36
See application file for complete search history.

(56) References Cited

U.S. PATENT DOCUMENTS

| | | | | |
|---|---|---|---|---|
| 1,728,542 | A | * | 9/1929 | Hames ............... A61C 17/0202 601/162 |
| 5,746,721 | A | * | 5/1998 | Pasch ................... A61M 3/022 604/152 |
| 2001/0012605 | A1 | * | 8/2001 | Kawamura ........ A61C 17/0202 433/29 |
| 2005/0004498 | A1 | * | 1/2005 | Klupt .................. A61C 17/222 433/80 |
| 2007/0203439 | A1 | | 8/2007 | Boyd et al. |
| 2008/0065001 | A1 | * | 3/2008 | DiNucci ............. A61M 3/0258 604/73 |
| 2010/0266980 | A1 | | 10/2010 | Boyd et al. |
| 2014/0193774 | A1 | | 7/2014 | Snyder et al. |
| 2014/0227659 | A1 | | 8/2014 | Thomas et al. |
| 2014/0272782 | A1 | * | 9/2014 | Luettgen ............ A61C 17/0205 433/80 |

(Continued)

*Primary Examiner* — Courtney B Fredrickson
(74) *Attorney, Agent, or Firm* — NGUYEN TARBET IP LAW

(57) ABSTRACT

An oral irrigator system having an ergonomic casing with a pliable nozzle assembly, and coupled to a detachable and refillable fluid reservoir. The ergonomic casing contains a power source and a pump mechanism. The detachable nozzle head delivers a pulsating jet of fluid with adjustable speed into the oropharyngeal cavity. When the system is turned on, the rechargeable battery activates the diaphragm pump to draw fluid from the reservoir using a fluid pipe and delivers the fluid to the tip of the nozzle head.

1 Claim, 7 Drawing Sheets

(56) References Cited

U.S. PATENT DOCUMENTS

2015/0173850 A1   6/2015  Garrigues et al.
2015/0182319 A1   7/2015  Wagner et al.
2018/0153666 A1   6/2018  Snyder et al.
2021/0307888 A1* 10/2021  Wagner .............. A61C 17/0202

* cited by examiner

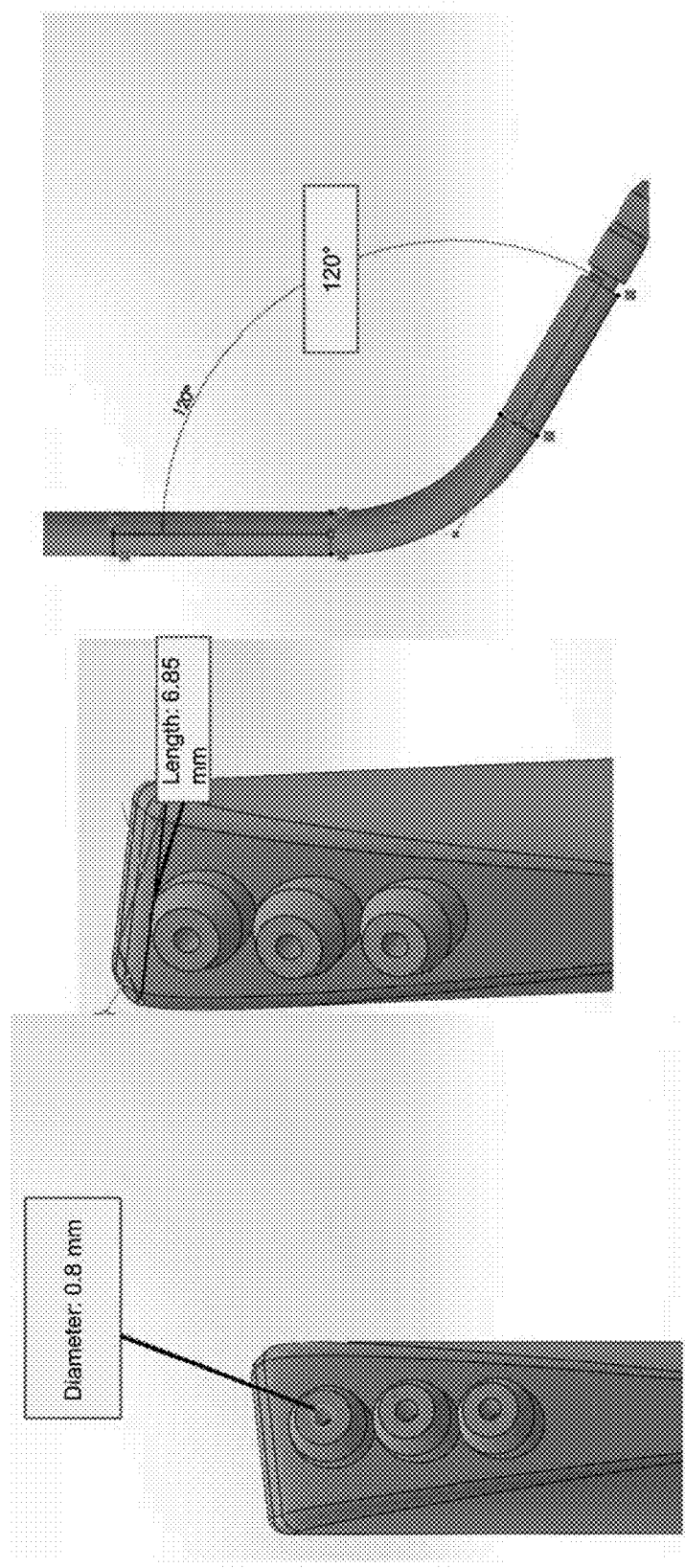

SYSTEM FOR IRRIGATING THE UPPER AERODIGESTIVE TRACT AND NEIGHBORING AREAS

CROSS-REFERENCES TO RELATED APPLICATIONS

This application is a non-provisional and claims benefit of U.S. Provisional Application No. 63/055,059 filed Jul. 22, 2020, the specification of which is incorporated herein in their entirety by reference.

FIELD OF THE INVENTION

The present invention relates to an oral irrigating device to irrigate the upper aerodigestive tract and the neighboring areas. More particularly, the present invention may comprise a system of components for irrigating the throat and neighboring areas such as, but not limited to, the tonsils.

BACKGROUND OF THE INVENTION

About 65 million Americans suffer from halitosis or bad breath at some point in their lives. A very common reason for halitosis is the entrapment of food debris and microorganisms in the palatine tonsils. The accumulation of debris and bacteria in the tonsillar crypts causes the formation of tonsil stones (FIG. 4A). The formation of these stones initiates by swelling (edema) of the tonsil due to the accumulation of debris and sulfur-producing bacteria. The swelling pushes the position of the tonsillar crypts farther from the surface, which leads to further bacteria and calcium accumulation. This leads to a foul-smelling hard debris called tonsillolith or tonsil stone. Due to the negative effects of halitosis on people's personal, family, and professional life, occasionally, patients will undergo a tonsillectomy surgery to eliminate tonsils stones.

Although tonsillectomy can be a solution in extreme cases, it is possible to prevent and treat tonsil stones without surgery. However, there are currently no means or products in the market that can be used on a daily basis by the consumer for clearing tonsil stones, preventing tonsil stone formation, and maintaining tonsil hygiene. Therefore, as recognized by the present invention, what is needed is an oral irrigation device that would directly fight the bad breath from the tonsils and tongue.

BRIEF SUMMARY OF THE INVENTION

It is an objective of the present invention to provide an oral irrigating device that improves the irrigation of an area of an upper aerodigestive tract and a plurality of neighboring areas, as specified in the independent claims. Embodiments of the invention are given in the dependent claims. Embodiments of the present invention can be freely combined with each other if they are not mutually exclusive.

In some aspects, the present invention features an oral irrigating device with a main body and detachable nozzle. The main body may house a power source and pump mechanism coupled to a fluid channel. A detachable and refillable reservoir is removably coupled to the main body and in fluid communication with the pump mechanism via the fluid channel. The reservoir may hold water blended with dissolvable tablets formulated to reduce bacterial growth and prevent tonsilloliths. The pliable irrigating nozzle may be configured with a plurality of insulated wires for convenient positioning of a nozzle tip having multiple jet head outputs. In further embodiments, the nozzle tip may further have a dedicated LED light that aids in visual ease for targeting different subsites of the oral cavity including, but not limited to, tonsil stones.

In some embodiments, the nozzle piece can have insulated metal wires that run through the entire device. The insulated wires can act as a backbone for the nozzle, while being pliable for the user to adjust to their optimal position by bending the nozzle piece. The insulated wires also serve as a medium to connect the LED light source to an integrated circuit (IC).

In other embodiments, the main body is ergonomic, water-resistant, and strong enough to withstand long-term usage without break-down. The main body also houses the integrated circuit (IC) or chip. The IC is programmed to respond to the user's settings (i.e., on/off button, pulse vibrating speed, etc.).

In some embodiments, the fluid reservoir can store sufficient amounts of fluid, e.g. about 300 mL, to allow the user to run a cleaning session of approximately 60 seconds on the highest flow rate setting. In some embodiments, dissolvable tablets containing about 10 mg of zinc and/or other minerals are added to the fluid. Zinc is anti-bacterial and can reduce overgrowth of bacteria in the tonsils and the mouth and help with reduced halitosis.

In some embodiments, the oral irrigating device can deliver a pulsating jet of water with adjustable speed that acts as a soft vibrating mechanism to ebb fluid into an oral cavity and crevices of the tonsils. Without wishing to limit the invention to any particular theory or mechanism, the pulsating jet of water may ebb fluid into the oral cavity at a plurality of angles at once. The oral irrigating device may further comprise a plurality of detachable and replaceable nozzles to satisfy and improve daily oral hygiene. In other embodiments, the oral irrigating device may comprise a handheld compartment that is portable and lightweight. None of the presently known prior references or works has the inventive technical features of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1 illustrates a hand-held oral irrigator with a detachable nozzle head, an ergonomic casing and a fluid reservoir, in accordance with an embodiment of the present invention.

FIG. 2 shows an exploded view of the ergonomic casing and fluid reservoir. The broken lines indicate components that are inside the casing. The dash-dot lines are fluid channels whereas the dot-dot lines are electrical connections.

Figure 1:
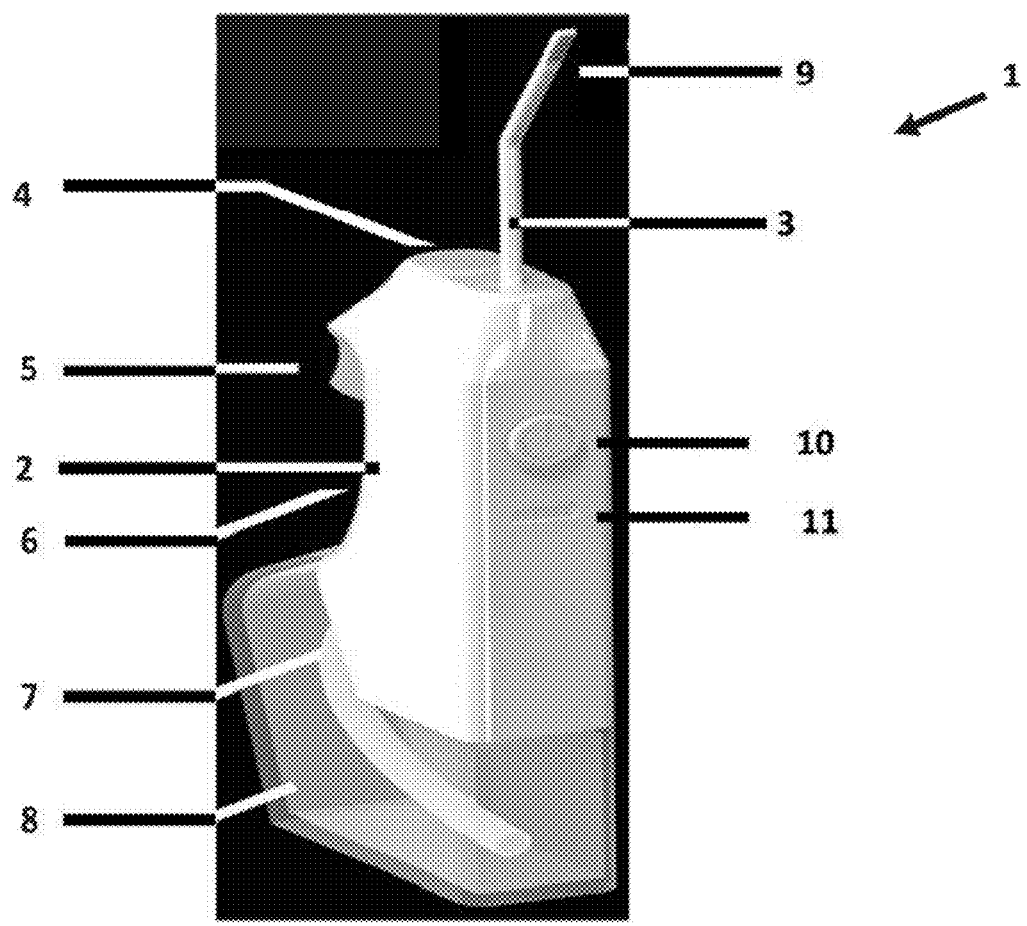

FIG. 10A shows a schematic of a preferred embodiment of the detachable nozzle of the presently claimed invention with measurements of the nozzle head diameter. FIG. 10B shows a schematic of a preferred embodiment of the detachable nozzle of the presently claimed invention with measurements of the nozzle tip width. FIG. 10C shows a schematic of a preferred embodiment of the detachable nozzle of the presently claimed invention with measurements of the angle of the nozzle.

DETAILED DESCRIPTION OF THE INVENTION

Following is a list of elements corresponding to a particular element referred to herein:
1 oral irrigator
2 main body
3 detachable nozzle
4 detach button
5 fluid pressure trigger
6 ergonomic grip
7 fluid channel
8 fluid reservoir
9 nozzle tip
10 on/off power button
11 battery indicator
12 metal wires
13 light
14 vibration control button
15 light control button
16 nozzle shaft
17 connector
18 shaft bend or kink
19 nozzle head
20 power source
21 pump
22 fluid compartment As used herein, the terms "treat", "treating", or "treatment" refer to both therapeutic treatment and prophylactic or preventative measures, with the objective of preventing, reducing, slowing down (lessen), inhibiting, eliminating or removing an undesired physiological change, symptom, disease, or disorder, such as the development or spread of tonsillolith or tonsil stones. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Optionally, the subject or patient may be identified (e.g., diagnosed) as one suffering from the disease or condition (e.g., tonsillolith or tonsil stones). Subjects with tonsillolith or tonsil stones can be identified by, for example, any or a combination of appropriate diagnostic methods known in the art.

According to some embodiments, the present invention features a device whose tip vibrates to massage the tissues in an area of an upper aerodigestive tract that includes a tongue and tonsils. In a preferred embodiment, a vibration frequency of the tip can be controlled and adjusted. In further embodiments, configured to be connected to another device that is placed on maxillary or mandibular teeth or gums.

Figure 2:
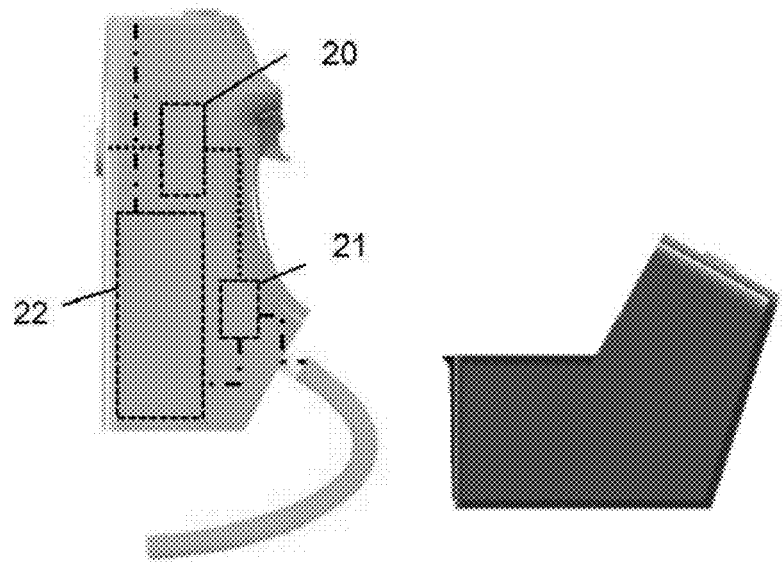
Figure 3:
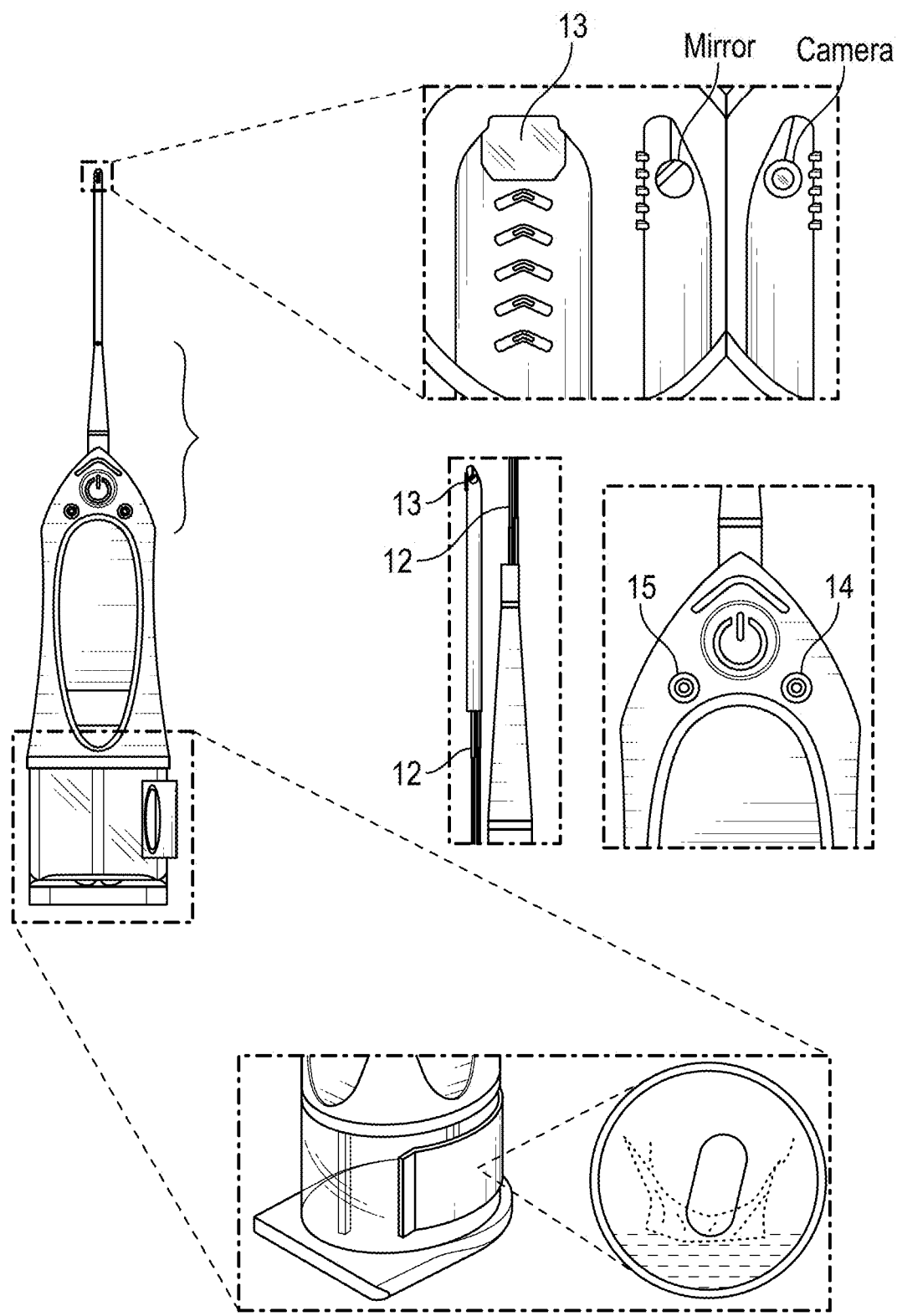
FIG. 3 illustrates another embodiment of the hand-held oral irrigator with close-up views of a light on a nozzle tip, controls, and the fluid reservoir.

Referring now to FIGS. 1-3, in some embodiments, the present invention features a hand-held oral irrigating device 1 with a main body 2 and a detachable nozzle 3. The main body may house a power source 20 and a pump mechanism 21 coupled to a fluid channel 7. In one embodiment, the power source 20 may be a rechargeable battery. In another embodiment, the pump mechanism 21 may be a miniature diaphragm pump. As shown in FIG. 2, a detachable and refillable reservoir 8 is removably coupled to the main body 1 and in communication with the pump mechanism via the fluid channel 7. The detachable nozzle 3 may deliver a pulsating jet of fluid with adjustable speed or pressure into an oropharyngeal cavity. In preferred embodiments, the device 1 is used to rinse a pharynx and its neighboring areas, and structures within the oral cavity. The oral irrigating device can remove or prevent oropharyngeal debris and tonsil stones. In some embodiments, a diameter of each nozzle head (19) may be configured to produce a fluid stream capable of cleaning an area of an upper aerodigestive tract. The diameter of each nozzle head can be configured to make the fluid stream narrow enough to prevent causing pain to a user while still efficiently cleaning the upper aerodigestive tract. The stream may have a width of about 0.1 to 3.0 mm. For example, the diameter of the nozzle head can make the fluid stream narrow enough to prevent causing pain to a user while still causing the fluid stream to flow at a sufficient pressure or flow rate for efficient cleaning.

Referring to FIG. 3, the reservoir 8 is configured to store the fluid. In some embodiments, the fluid may comprise electrolytes, vitamins, minerals, antiseptic, alcohol, medication, or a combination thereof. Preferably, the fluid has antibacterial properties and is anti-inflammatory. For example, the reservoir may hold water blended with a plurality of dissolvable tablets formulated to reduce bacterial growth and prevent tonsilloliths. In other embodiments, the fluid has an inert chemical and physiological characteristic.

In one embodiment, as shown in FIG. 1, a rear end of the main body may contain a fluid pressure trigger 5 that when pulled increases a pressure of the fluid that is pumped into the oral cavity. In another embodiment, the main body may include an indentation or curvature that provides an ergonomic grip 6. In some embodiments, a distal end of the main body may include a detach button 4 that activates detachment of the nozzle head from the main body.

In some embodiments, as shown in FIG. 2, the rechargeable battery 20, depending on the state of the control, can activate the pumping mechanism 21, e.g. diaphragm pump, to draw fluid from the reservoir 8 using a fluid channel 7 and deliver the fluid to a cleaning tip 9 of the nozzle. In other embodiments, as referenced in FIG. 3, a front side of the main body may include an on/off 10 control to activate or deactivate a motor and a battery indicator 11 that indicates a remaining battery charge.

In some embodiments, the front side of the main body of the oral irrigator may include a control button 14 to activate a soft vibrating mechanism to ebb the fluid into an oral cavity and crevices of tonsils. In other embodiments, the main body may also include a light control button 15 to turn on/off a display light 13, camera, or mirror disposed at the cleaning tip 9 of the nozzle as shown in FIG. 3.

In some embodiments, as shown in FIG. 2, a fluid compartment 22 may be disposed in the main body of the invention. The fluid compartment 22 may be designed for balanced weight when holding the fluid. In some embodiments, a lower portion of the fluid reservoir 8 may be shaped to have a stable platform when the oral irrigator is placed in a vertical orientation on a surface.

Figure 5:
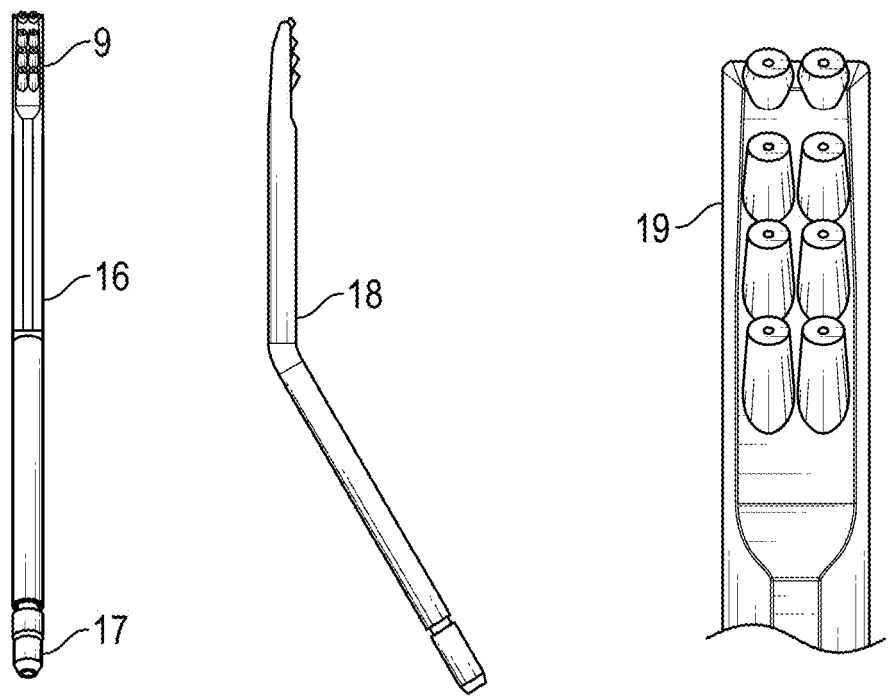
FIG. 5 shows front and side views of the detachable nozzle, and a close-up view of the nozzle head, in accordance with an embodiment of the present invention.

Referring to FIG. 5, the detachable custom irrigating nozzle may have a shaft 16 that has the cleaning tip 9 positioned at a distal end and a connector 17 positioned at a posterior end thereof. The connector allows for the nozzle to be removable attached to the main body (2). Referring to FIG. 3, the nozzle may have insulated metal wires 12 that run through them. In one embodiment, the shaft 16 may be pliable for convenient positioning, and the metal wires 12 can act as a backbone. Without wishing to limit the invention, the user can adjust the nozzle to an optimal cleaning position by bending the nozzle piece. For example, FIG. 5 shows the nozzle shaft 16 with a bend or kink 18. In other embodiments, the insulated wires may also serve as a medium to connect an LED light 13 source, camera, or mirror on the distal end of the nozzle piece to an integrated circuit chip in the main body 2 of the oral irrigator.

Figure 6:
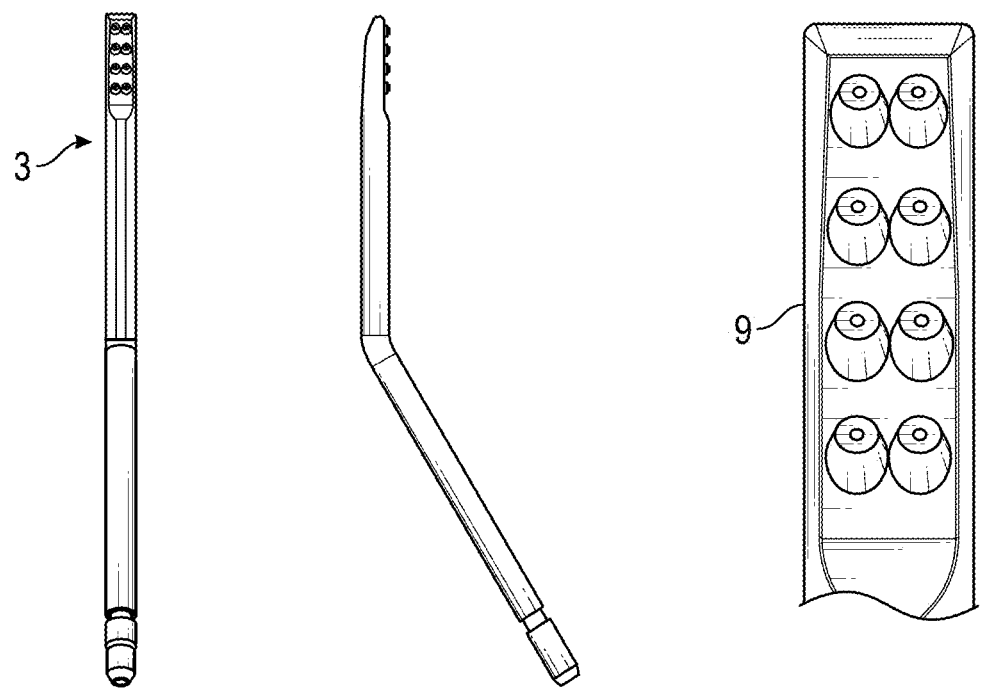
FIG. 6 shows front and side views of the detachable nozzle, and a close-up view of the nozzle head, in accordance with another embodiment of the present invention.

Various embodiments of the tip 9 of the nozzle are shown in FIGS. 5-8. In some embodiments, the tip 9 may be flat or raised. In other embodiments, the tip 9 can be made of a soft material or a hard material. In some embodiments, the tip 9 may have a flat surface. For example, FIGS. 5-6 show embodiments of the tip having a flat surface. In one embodiment, the nozzle tip can have a width of about 0.5-1.5 cm. In another embodiment, the nozzle tip can have a length of about 0.5-2.5 cm.

Figure 7:
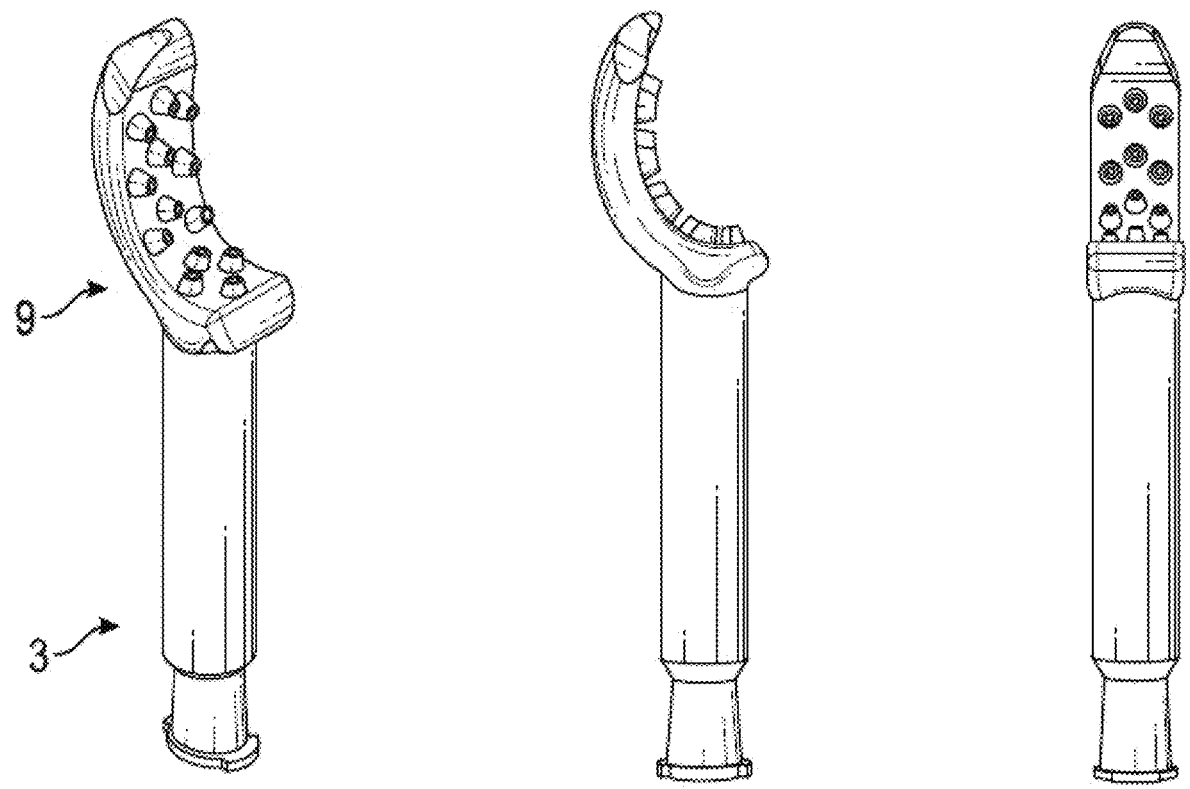
FIG. 7 shows perspective, side, and front views of the detachable nozzle according to another embodiment of the present invention.
Figure 8:
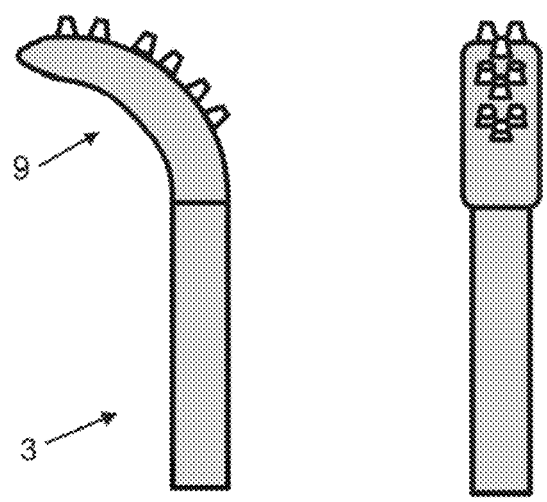
FIG. 8 shows side and front views of the detachable nozzle according to another embodiment of the present invention.

In other embodiments, the nozzle tip 9 may have a curved surface as shown in FIGS. 7-8. For instance, the nozzle tip 9 has a crescent shape. In a non-limiting embodiment, FIG. 7 shows a nozzle tip with a concave curvature. In another embodiment, FIG. 8 shows a nozzle tip with a convex curvature. In some embodiments, the nozzle tip has a curvature that has an arc angle/measure ranging from about 90° to about 120°. In other embodiments, the nozzle tip has an arc length ranging from about 1-3 cm and a width of about 0.5-1.5 cm.

In some embodiments, a plurality of nozzle heads 19 may be disposed on the nozzle tip. The nozzle heads are the outputs for ejecting fluid from the nozzle and into the mouth. In one embodiment, the plurality of nozzle heads project from the surface of the nozzle tip perpendicularly or at an angle. The angle of the nozzle heads may be uniform or the nozzle heads may be angled in different directions. The number of nozzle heads may range from about 6 to 12 heads. Without wishing to limit the invention, the nozzle heads are oriented in such a way to maximize cleaning efficiency. In further embodiments, the irrigating devices described herein can be configured to connect to another device that is placed on maxillary or mandibular teeth or gums.

Figure 4A:
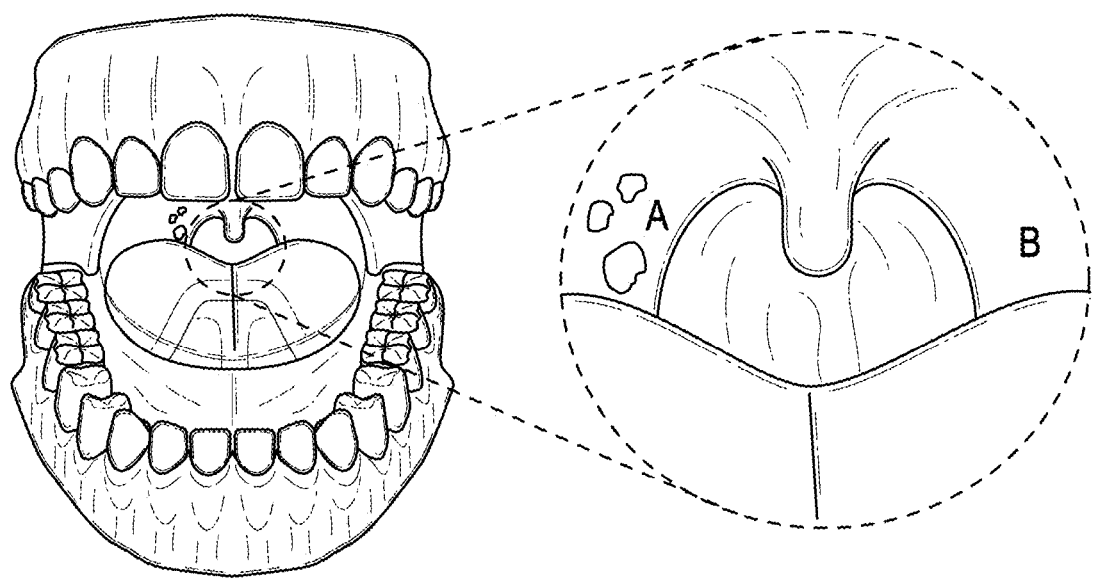
FIG. 4A shows an interior view of a mouth with tonsil stones (A) and a healthy tonsil (B).
Figure 4B:
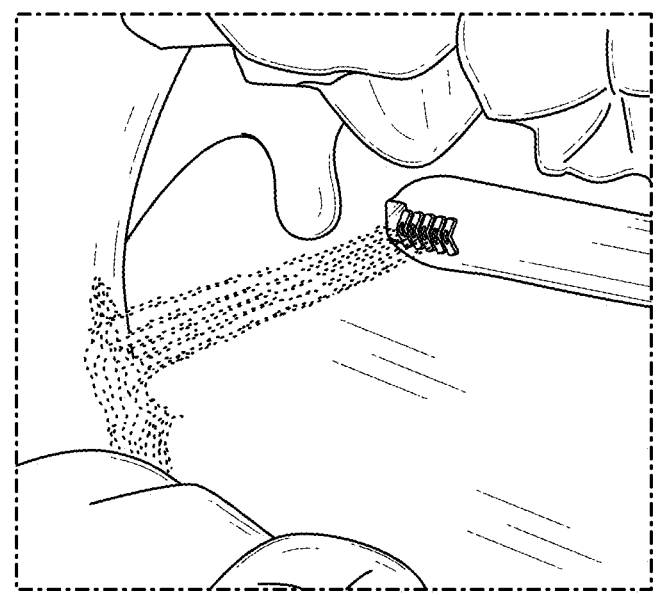
FIG. 4B illustrates how the hand-held oral irrigator is used to clean the tonsils.

Referring to FIGS. 4A-4B, the oral irrigator device (1) described herein may be used to treat tonsil stones in a subject in need thereof. The treatment process may comprise inserting the irrigating nozzle (3) inside the subject's mouth such that the nozzle tip (9) is positioned near a tonsil, and pulsating a fluid through the nozzle heads (19) and into an oral cavity and crevices of the tonsils, thereby removing the tonsil stones and/or preventing recurrence thereof.

According to another embodiment, the oral irrigator device (1) described herein may be used to treat halitosis in a subject in need thereof. The method may comprise inserting the irrigating nozzle (3) inside the subject's mouth, and pulsating a fluid through the nozzle heads (19) to wash or rinse the subject's tonsils, tongue, teeth, gums, and/or back of throat, including an oral cavity and crevices of the tonsils, thereby eliminating sources of bad breath at the tonsils, tongue, and back of the throat. Alternatively or in conjunction, the methods described herein can also treat inflammation and/or infection inside the subject's mouth.

The present invention features an oral irrigator device (1). In some embodiments, the device (1) may comprise a main body (2) comprising a pump (21) disposed therein, an irrigating nozzle (3) attached to the main body (2) and in fluidic communication with the pump (21), the irrigating nozzle (3) comprising a plurality of nozzle heads (19) disposed at a tip (9) of the irrigating nozzle, a detach button (4) disposed on a distal end of the main body (2) for activating detachments of the plurality of nozzle heads (19) from the main body (2), a fluid pressure trigger (5) disposed on a rear end of the main body (2) for increasing a pressure of a fluid pumped by the pump (21) when pulled, an ergonomic grip (6) disposed on the main body (2), an on/off control (10) disposed on a front side of the main body (2) capable of activating and deactivating the oral irrigator device (1), a battery indicator (11) for indicating a remaining battery charge, and a refillable reservoir (8) fluidly coupled to the main body (2) and in fluid communication with the pump (21) via a fluid channel (7). In one embodiment, the refillable reservoir (8) may be removably attached to the main body (2). In another embodiment, the refillable reservoir (8) may be separate from the main body (2). The refillable reservoir (8) may be used while attached or separate from the main body (2).

Figure 9:
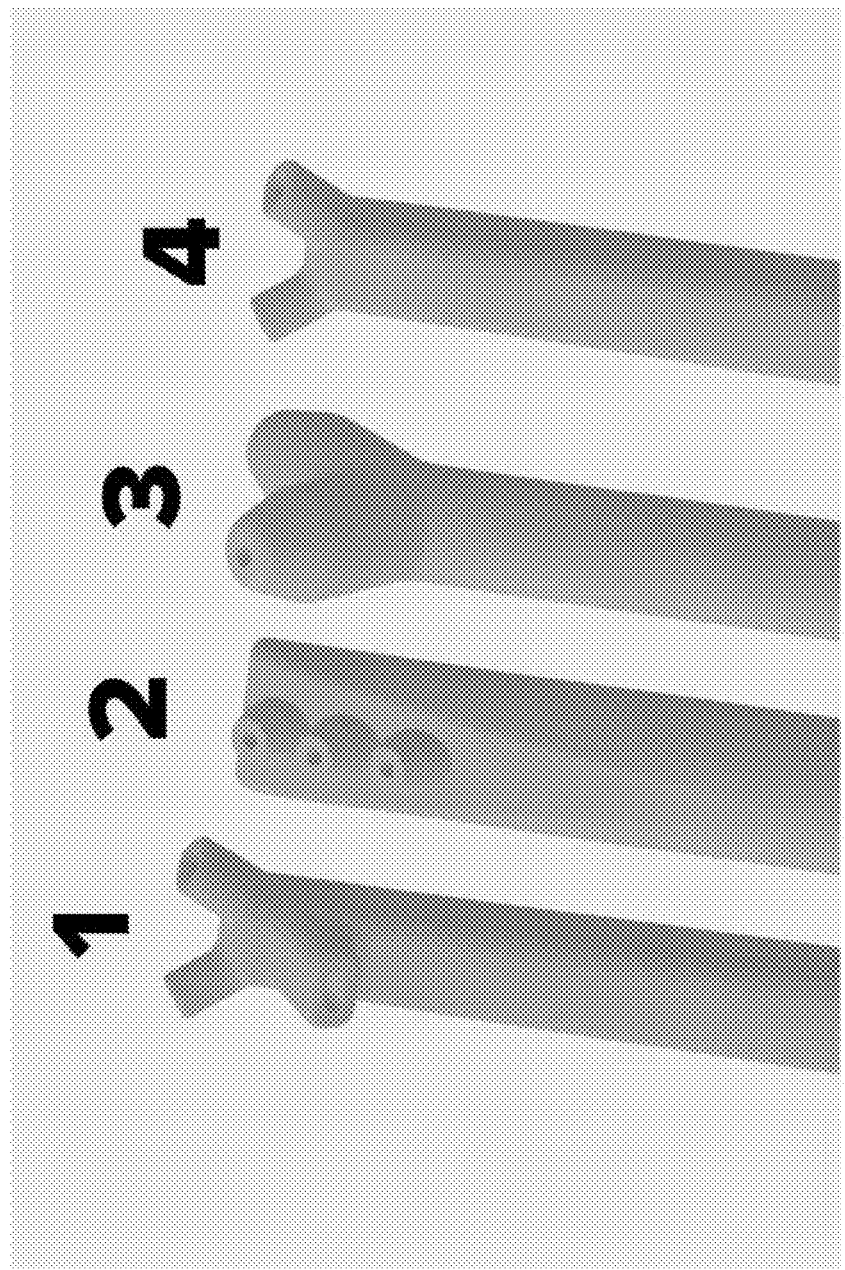
FIG. 9 shows various embodiments of the detachable nozzle of the presently claimed invention.

The pump (21) may be configured to pump the fluid from the reservoir (8), through the fluid channel (7) and the irrigating nozzle (3), and eject said fluid from the nozzle heads (19). A flow rate of the pump (21) may be adjustable to optimize the flow rate for cleaning. The nozzle heads (19) may be configured to direct the fluid onto a surface at various angles. According to some embodiments, the plurality of nozzle heads (19) may be arranged in a vertical line configuration (see FIGS. 9-10). The nozzle tip (9) may vibrate to massage tissues in the area of the upper aerodigestive tract that includes a tongue and tonsils. The fluid may comprise electrolytes, vitamins, minerals, antiseptic, alcohol, medication, or a combination thereof.

A diameter of each nozzle head of the plurality of nozzle heads (19) may be configured to produce a stream capable of cleaning an area of an upper aerodigestive tract. The diameter of each nozzle head can be configured to make the fluid stream narrow enough to prevent causing pain to a user while still efficiently cleaning the upper aerodigestive tract. The stream may have a width of about 0.1 to 3.0 mm.

In some embodiments, the device (1) may further comprise a light (13), camera, or mirror disposed at the tip (9) of the irrigating nozzle (see FIG. 3). In some embodiments, the nozzle heads (19) may be oriented at varying angles relative to the surface of the nozzle tip (9). In some embodiments, the surface of the nozzle tip (9) may be flat. In some embodiments, the surface of the nozzle tip (9) may be curved such that the nozzle heads (19) are oriented in varying angles. In some embodiments, the tip may be angled, curved or straight with the nozzle heads (19) configured to direct and spray a fluid. In some embodiments, the device (1) may be used to remove or prevent oropharyngeal debris and tonsil stones, rinse a pharynx and its neighboring areas, rinse a structure within the oral cavity, and/or treat inflammation and/or infection. In some embodiments, the nozzle tip (9) may be flat or raised and is configured to touch tissues. In some embodiments, a vibration frequency of the tip may be controlled and adjusted. In some embodiments, the nozzle heads (19) may vary in height. In some embodiments, the nozzle tip (9) may be made of a hard or soft material. In some embodiments, the device (1) may be configured to be connected to another device that is placed on maxillary or mandibular teeth or gums. In some embodiments, the minerals may include calcium, zinc, magnesium, or a combination thereof. In some embodiments, the fluid may have antibacterial properties and is anti-inflammatory, may have an inert chemical and physiological characteristic, and/or comprise a tablet dissolved in a solvent. The solvent may be water or alcohol. In some embodiments, the diameter of each nozzle head of the plurality of nozzle heads (19) may be 0.5 to 1 mm.

In some embodiments, the diameter of each nozzle head of the plurality of nozzle heads (19) may be 0.5 to 0.75 mm. In some embodiments, the diameter of each nozzle head of the plurality of nozzle heads (19) may be 0.75 to 0.85 mm. In some embodiments, the diameter of each nozzle head of the plurality of nozzle heads (19) may be 0.85 to 1 mm. In some embodiments, the diameter of each nozzle head of the plurality of nozzle heads (19) may be 0.8 mm. In some embodiments, a width of the nozzle tip (9) may be 6 to 7.5 mm. In some embodiments, a width of the nozzle tip (9) may be 6 to 6.5 mm. In some embodiments, a width of the nozzle tip (9) may be 6.5 to 7 mm. In some embodiments, a width of the nozzle tip (9) may be 7 to 7.5 mm. In some embodiments, a width of the nozzle tip (9) may be 6.62 mm. In some embodiments, an angle of the tip (9) may be 100 to 140 degrees. In some embodiments, an angle of the tip (9) may be 100 to 110 degrees. In some embodiments, an angle of the tip (9) may be 110 to 130 degrees. In some embodiments, an angle of the tip (9) may be 130 to 140 degrees. In some embodiments, an angle of the tip (9) may be 120 degrees.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. All the directional references here are made to aid in the reader's understanding of the present invention, and do not create limitations, particularly as to the position, orientation, or use of the invention. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An oral irrigator device (1) comprising:
   a. a main body (2) comprising a pump (21) disposed therein;
   b. an irrigating nozzle (3) attached to the main body (2) and in fluidic communication with the pump (21), the irrigating nozzle (3) comprising a plurality of nozzle heads (19) disposed at a tip (9) of the irrigating nozzle, wherein the plurality of nozzle heads (19) are arranged in a vertical line configuration, and wherein the tip (9) of the irrigating nozzle (3) is configured to vibrate;
   c. a detach button (4) disposed on a distal end of the main body (2) for activating detachments of the plurality of nozzle heads (19) from the main body (2);
   d. a fluid pressure trigger (5) disposed on a rear end of the main body (2) for increasing a pressure of a fluid pumped by the pump (21) when pulled;
   e. an ergonomic grip (6) disposed on the main body (2);
   f. an on/off control (10) disposed on a front side of the main body (2) capable of activating and deactivating the oral irrigator device (1);
   g. a battery indicator (11) for indicating a remaining battery charge; and
   h. a refillable reservoir (8) fluidly coupled to the main body (2) and in fluid communication with the pump (21) via a fluid channel (7);
      wherein the pump (21) is configured to pump the fluid from the reservoir (8), through the fluid channel (7) and the irrigating nozzle (3), and eject said fluid from the nozzle heads (19),
      wherein a flow rate of the pump (21) is adjustable to optimize the flow rate for cleaning,
      wherein the nozzle heads (19) are configured to direct the fluid onto a surface at various angles,
      wherein a diameter of each nozzle head of the plurality of nozzle heads (19) is configured to produce a stream capable of cleaning an area of an upper aerodigestive tract,
      wherein the tip (9) of the irrigating nozzle (3) vibrates to massage tissues in the area of the upper aerodigestive tract that includes a tongue and tonsils,
      wherein the fluid comprises electrolytes, vitamins, minerals, antiseptic, alcohol, medication, or a combination thereof.

* * * * *